United States Patent [19]

Atwood et al.

[11] 4,021,123
[45] May 3, 1977

[54] HEAT EXCHANGER FOR ANALYSIS APPARATUS

[75] Inventors: John G. Atwood, Redding; Charles F. Demey, II, W. Redding, both of Conn.

[73] Assignee: The Perkin-Elmer Corporation, Norwalk, Conn.

[22] Filed: Jan. 22, 1976

[21] Appl. No.: 651,542

Related U.S. Application Data

[63] Continuation of Ser. No. 499,853, Aug. 22, 1974, abandoned.

[52] U.S. Cl. .................... 356/244; 356/246
[51] Int. Cl.² ............. G01N 21/26; G01N 1/10
[58] Field of Search ............... 73/15 B, 190 R; 23/253 R, 254 R, 259; 356/246, 244

[56] References Cited

UNITED STATES PATENTS

| | | | |
|---|---|---|---|
| 1,835,985 | 12/1931 | Henri | 356/246 |
| 3,339,398 | 5/1967 | Barrall et al. | 73/15 |
| 3,467,501 | 9/1969 | Groszek | 73/190 |
| 3,552,207 | 1/1971 | Monk et al. | 73/190 |
| 3,718,437 | 2/1973 | Paloniemi | 73/190 |
| 3,740,194 | 6/1973 | Hendy | 73/15 |
| 3,854,848 | 12/1974 | Kiesow | 23/253 |

*Primary Examiner*—Herbert Goldstein
*Attorney, Agent, or Firm*—S. A. Giarratana; F. L. Masselle

[57] ABSTRACT

A heat exchanger for photometric analysis apparatus in which a sample to be analyzed is brought through a thermostated metal block to a sample cell made of highly conductive material, the sample cell being contained within a cavity atop the block and thermally isolated therefrom whereby the sample is preheated to a desired temperature and remains at that temperature within the sample cell during a predetermined analysis period.

6 Claims, 2 Drawing Figures

HEAT EXCHANGER FOR ANALYSIS APPARATUS

This application is a continuation of our copending application Ser. No. 499,853, filed Aug. 22, 1974 (now abandoned).

BACKGROUND OF THE INVENTION

This invention relates to photometric analysis apparatus in general and more particularly to an improved heat exchange apparatus for use in such apparatus. In a copending application of John G. Atwood et al for U.S. Letters Patent, Ser. No. 594,951, filed July 10, 1975 as a continuation of now abandoned application Ser. No. 499,602, filed Aug. 22, 1974, and assigned to the same assignee as the present invention, there is disclosed a completely automated analysis apparatus for the photometric determination of enzymes in human serum. The determination involves the dilution of the serum and the admixture of two reagents. The reaction mixture is then transferred to the sample cell of a photometer for analysis; specifically, the rate of change of absorbance of the reaction mixture (which is a function of the concentration of the particular enzyme sought) is photometrically determined. In such apparatus, and other similar apparatus, accuracy of results requires that the sample in the photometer cell be maintained at a substantially constant predetermined temperature during the photometric analysis period. It is important first of all that the sample be at a particular temperature within certain tolerances. It is more important, however, that the sample temperature not change during the absorbance measurement period. Thus, to maintain the required accuracy in such apparatus, means are needed to bring the sample up to at least an approximation of a predetermined temperature and to ensure that the sample stays at that temperature throughout the measurement period.

SUMMARY OF THE INVENTION

The present invention provides such heat exchanger means. The photometer sample cell is contained within a cavity atop a thermostated metal block. The sample to be analyzed is brought in through the thermostated metal block during which time, it is brought to the desired temperature. The cell itself is supported in the cavity by means which isolate the cell from the thermostated block so that it is not subject to rapid temperature changes which might occur in the block itself. The cell is made of silver or another metal of high thermal conductivity so that in a short period the temperature of the cell and, concomitantly, the sample therein reach an equilibrium and remain at an essentially constant temperature during the period of photometric analysis.

DETAILED DESCRIPTION OF THE PREFERRED EMBODIMENT

Figure 1:
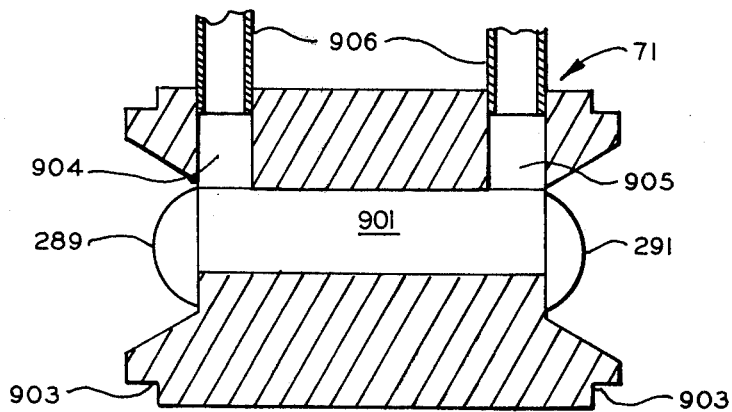
FIG. 1 is a detailed axial section of a photometer sample cell for use in the present invention.

FIG. 1 illustrates a photometer sample cell 71 constructed according to the present invention. The photometer cell itself is made of silver and defines a sight passage 901 in which the sample rests during analysis. The ends of passage 901 are closed by lens-shaped members 289 and 291 which form part of the photometer optical system shown and described in detail in the aforementioned copending patent application as well as another copending application of John G. Atwood et al for U.S. Pat., Ser. No. 499,617 filed Aug. 22, 1974, and assigned to the same asignee as the present invention. For present purposes, suffice it to say that members 289 and 291 permit transmission of a beam of radiation axially through passage 901 for the performance of the photometric analysis of the sample contained therein. Cell 71 is essentially cylindrical in its external configuration and is provided with cutouts 903 for resting the cell in a plastic block as will be described presently. Openings 904 and 905 are provided in the cell 71 in flow communication with the respective ends of passage 901, enabling the introduction and removal of a reaction sample. The transfer of a reaction sample to cell 71 may be effected by means of a transfer system described and claimed in a copending application to John G. Atwood et al for U.S. Pat., Ser. No. 499,618, filed Aug. 22, 1974, and assigned to the same assignee as the present invention. Inserted into each of the openings 904 and 905 is a stainless steel nipple 906.

As already mentioned, cell 71 is made of silver but in general any material of high thermal diffusivity may be used. The diffusivity must be such that the time for equalibrium in the cell is short as compared to the time required to transfer the sample through the heat exchanger described below to the cell. While it is important that the sample be maintained at a particular temperature during measurement, it is more important that the temperature remain constant during analysis. For example, it may be sufficient if the temperature of the sample in the cell is within 0.2° C of the desired temperature, 30° C. For a particular enzyme determination; however, the temperature during analysis period should not vary more than 0.01° C.

Figure 2:
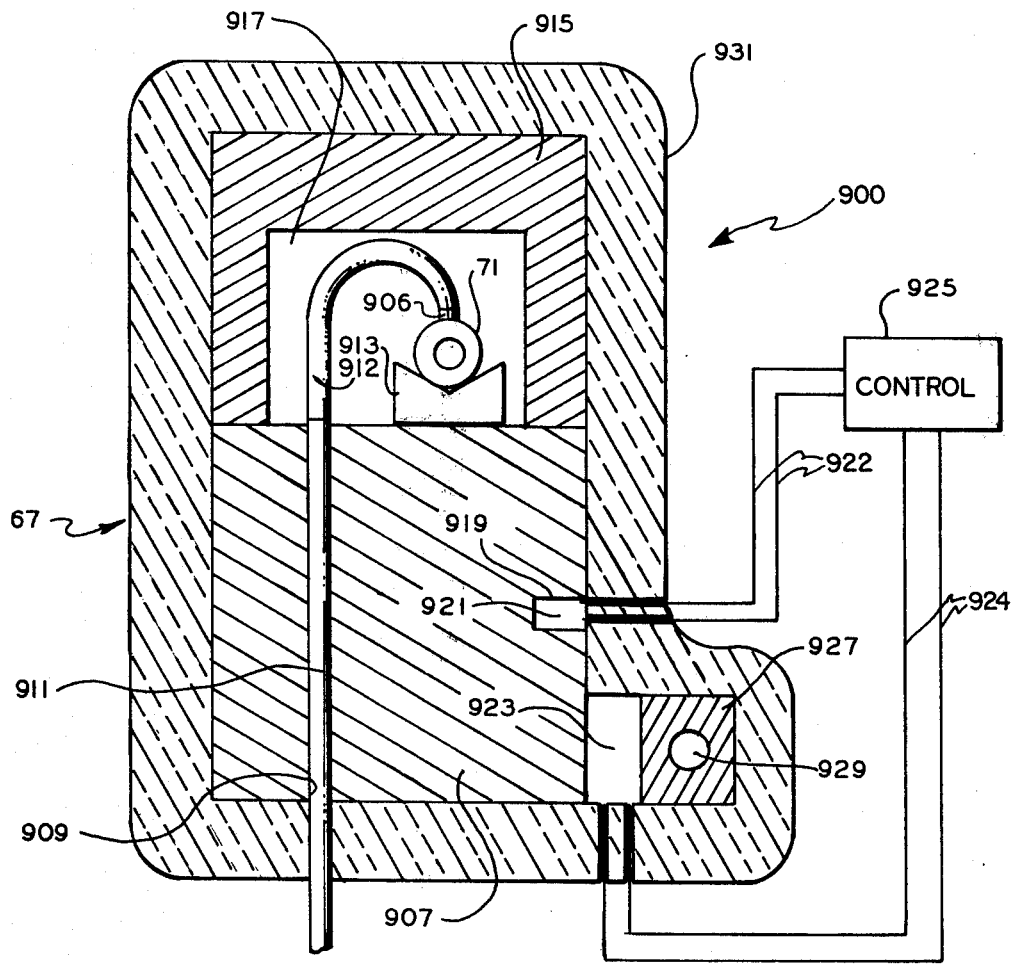
FIG. 2 is a cross-sectional view of the heat exchanger of the present invention.

FIG. 2 shows heat exchanger assembly 900 for bringing the sample to a desired temperature and maintaining it at that temperature. The assembly comprises a base block 907 made of aluminum and containing a tubular passage 909 within which is inserted a stainless steel tube 911. The upper end of tube 911 is connected through Tygon tubing 912 to the sample cell nipple 906, at the inlet of sight passage 901. Cell 71 rests on a plastic V block 913, having good thermal insulation properties, located on top of the block 907. A cover 915, also of aluminum, is placed over the block 907 and bolted in place. Cover 915 and the top surface of block 907 coact to define a cavity 917 containing V-block 913, sample cell 71, and a portion of the associated tubing.

A recess 919 in block 907 accommodates insertion of a thermistor 921. Attached to the side of the block 907 below the thermistor 921 is a heat pump 923 which preferably takes the form of a Peltier device such as Borg Warner part No. 930-17. Leads 922 from thermistor 921 are connected to a control device 925 which provides outputs over leads 924 to operate the heat pump 923 in convnetional fashion. On the opposite side of heat pump 923 with respect to block 907 is a further metal block 927 having a passage 929 through which water is circulated to remove heat from the heat pump when it is operating in a cooling mode. The entire assembly is surrounded with insulation. In operation, heat pump 923 adjusts the temperature of the aluminum block 907 to the desired value. This results in the temperature in cavity 917 being approximately at the desired value, i.e., it is close enough to this value to provide accurate results. However, as noted above, the sample must not change its temperature during measurement. The use of the silver cell and its thermal isolation from block 907, by means of the Tygon tube connection 912 between tube 911 and nipple 906 as well as the plastic V block 913, assures the requisite temperature invariance. The high thermal conductivity of the silver causes it to reach an equilibrium temperature with the sample very quickly. Heat pump 923 proportionally changes the temperature of the aluminum block slightly, e.g., as the temperature of the block drops a small amount, the heat pump will increase its heat flow to bring it up to the set value. The block temperature does not vary much but even a small variation would be sufficient to affect the accuracy of the photometric analysis if experienced at the sample cell.

Thus, an improved heat exchanger for use in analysis apparatus has been shown. Although specific embodiments have been illustrated and described, it will be obvious to those skilled in the art that various modifications may be made without departing from the spirit of the invention which is intended to be limited solely by the appended claims.

What is claimed is:

1. In a photometer analysis system including means to transfer a reaction sample to a sample cell, apparatus for bringing the reaction sample to a predetermined temperature and maintaining its temperature constant in said cell comprising:

a. a metal block and cover of high thermal conductivity metal coacting to define a cavity, said cover and block being surrounded with thermal insulation;
   b. a photometer sample cell of high thermal conductivity metal containing a sight passage;
   c. thermal-insulation support means on said block mounting said sample cell in said cavity;
   d. a heat exchange tube extending through said block and into said cavity;
   e. conduit means of substantially lower thermal conductivity than said heat exchange tube interconnectng said sight passage with said heat exchange tube to thermally isolate the cell from said metal block; and
   f. temperature regulation means for maintaining said block at a substantially constant predetermined temperature.

2. Apparatus according to claim 1 wherein said temperature regulation means comprises:

a. means to sense the temperature of said block;
   b. a heat pump attached to said block to supply and remove heat to and from the block; and
   c. control means having an input from said temperature sensing means and providing an output to control said heat pump.

3. Apparatus according to claim 2 wherein said thermal insulation means comprise a plastic V-block on which said sample cell rests.

4. Apparatus according to claim 3 wherein said sample cell is made of silver.

5. Apparatus according to claim 4 wherein said block and cover are made of aluminum.

6. Apparatus according to claim 1 wherein said heat exchange tube is made of stainless steel and said conduit means is a tube made of Tygon.

* * * * *